US010935534B2

(12) United States Patent
Pauls et al.

(10) Patent No.: US 10,935,534 B2
(45) Date of Patent: Mar. 2, 2021

(54) WHOLE PLANT GAS EXCHANGE CHAMBER USING PRESSURIZATION AND VENTILATION OF SEPARATED CANOPY AND ROOT ZONES

(71) Applicant: BioChambers Incorporated, Winnipeg (CA)

(72) Inventors: Robert Barry Pauls, Winnipeg (CA); Marc Albert Joseph Theroux, Grande Pointe (CA); Patrick Calvin Friesen, Winnipeg (CA); Ronald Rowland Sugden, Beausejour (CA); Bruce Kettner, Winnipeg (CA)

(73) Assignee: BioChambers Incorporated, Winnipeg (CA)

( * ) Notice: Subject to any disclaimer, the term of this patent is extended or adjusted under 35 U.S.C. 154(b) by 158 days.

(21) Appl. No.: 15/723,292

(22) Filed: Oct. 3, 2017

(65) Prior Publication Data

US 2018/0113104 A1    Apr. 26, 2018

Related U.S. Application Data

(60) Provisional application No. 62/413,049, filed on Oct. 26, 2016.

(51) Int. Cl.
*G01N 33/00* (2006.01)
*A01G 7/02* (2006.01)
(Continued)

(52) U.S. Cl.
CPC .......... *G01N 33/0098* (2013.01); *A01G 7/02* (2013.01); *A01G 9/026* (2013.01); *A01G 24/50* (2018.02); *A01G 31/00* (2013.01)

(58) Field of Classification Search
CPC ...... G01N 33/0098; A01G 7/02; A01G 24/50; A01G 9/026
See application file for complete search history.

(56) References Cited

U.S. PATENT DOCUMENTS

| 6,860,163 B2 | 3/2005 | Tocquin et al. |
| 2012/0011773 A1* | 1/2012 | Cross ..................... A01G 9/026 47/65.8 |

FOREIGN PATENT DOCUMENTS

| CN | 2854556 U | 3/2007 |
| JP | 2005333921 | 8/2005 |
| WO | WO-2016061672 A1 * | 4/2016 ............. A01G 25/16 |

* cited by examiner

*Primary Examiner* — Lisa M Caputo
*Assistant Examiner* — Alex T Devito
(74) *Attorney, Agent, or Firm* — Kyle R Saherthwaite; Michael R William; Ade & Company Inc.

(57) ABSTRACT

A whole plant gas exchange apparatus employs a chamber having a first region for accommodating a growth medium and a root system of a whole plant, and a second region accommodating a canopy of the plant. The regions are separated by a barrier, except for an opening through which the stem of the plant is accommodated. An air source supplies incoming air to the second region through an intake. An air outlet conveys outgoing air from the second region to a gas sensor for analysis of the outgoing air after photosynthetic interaction with the plant canopy. A vent communicates the first region of the chamber to an ambient environment outside the chamber. A resulting pressurized state of the second region is used to exhaust air from the first region through the vent in order to isolate this exhausted air from the analyzed canopy air.

19 Claims, 2 Drawing Sheets

(51) Int. Cl.
*A01G 24/50* (2018.01)
*A01G 9/02* (2018.01)
*A01G 31/00* (2018.01)

WHOLE PLANT GAS EXCHANGE CHAMBER USING PRESSURIZATION AND VENTILATION OF SEPARATED CANOPY AND ROOT ZONES

CROSS REFERENCE TO RELATED APPLICATIONS

This application claims benefit under 35 U.S.C. 119(e) of Provisional Application Ser. No. 62/413,049, filed Oct. 26, 2016.

FIELD OF THE INVENTION

The present invention relates generally to gas exchange chambers used to measure photosynthetic performance or other plant/air interactions, and more particularly to a unique chamber design and associated method in which the growth medium and roots in one region of the chamber are at least semi-isolated from the canopy of the plant in another region of the chamber by a $CO_2$-impermeable barrier, while a pressurized state of the canopy region is used to exhaust air from the other region through a separate vent in order to isolate this exhausted air from the analyzed canopy air.

BACKGROUND

It is known to use measurement of carbon dioxide consumption by plants in order to measure various characteristics of a plant, including growth performance, and photosynthetic and respiratory efficiency.

One type of equipment used for such measurements is a single-leaf gas exchange system, which employs a handheld unit clamped onto a singular plant leaf. A major drawback of such systems is that extrapolation of whole-plant performance from a single-leaf measurement leaves much to be desired in terms of the overall complexity of the analysis and the accuracy of the results.

To address such shortcomings, whole plant gas exchange systems have also been proposed, where a chamber contains the entirety of the plant, thereby avoiding the need to extrapolate from single-leaf results.

However, it has been realized that while measurement of a whole plant approach avoids the need for extrapolation from single-leaf measurements, the whole plant approach introduces other complications, including the fact that soil and root-level respiration will have some effect on the measured results, whereas in at least some cases, it is desirable to measure the performance of only the canopy of the plant (i.e. the above ground portion of the plant).

It has therefore been proposed to use split-chamber designs where the chamber is divided into separate upper and lower compartments intended to isolate the canopy of the plant from the roots and the soil or other growth medium.

Examples of such split-compartment chambers are found in JP2005333921 and CN2854556U. The latter reference uses mating meniscuses to create small apertures through which the plant stems can pass, and requires application of a silica gel to attain an air-tight seal between the stems and meniscuses. The former reference likewise describes application of sealing material around the plant stalk at the surrounding divider between the two compartments in order to maintain airtight separation therebetween.

U.S. Pat. No. 6,860,163 discloses a chamber having a perforated base plate through which the stems of plants reach upwardly into the chamber from cylindrical support tubes that contain inert agar gel and hang down into a container of hydroponic growth medium.

There remains room or improvements and alternatives for isolating the plant's root system and growth medium from gas exchange analysis of the plant's canopy, and Applicant has developed a unique solution for same.

SUMMARY OF THE INVENTION

According to a first aspect of the invention, there is provided a whole plant gas exchange apparatus comprising:
a chamber having an interior space containing, or arranged to contain, a whole plant and an associated growth medium therein, said interior space including a first region for accommodating said growth medium and a root system of said whole plant established within said growth medium, and a second region for accommodating a canopy of said whole plant;
a barrier separating said first and second regions of the interior space from one another;
an opening between the first and second regions of the interior space to accommodate receipt of a stem of said whole plant through said opening to reach from the root system in the first region to the canopy in the second region;
an air intake communicating with the interior space of the chamber outside the first region and being connected or connectable to an air source for supplying incoming air to said second region of the interior space;
an air outlet communicating with the second region of the interior space to convey outgoing air from the second region to a gas sensor for analysis of said outgoing air after photosynthetic interaction with the canopy of the whole plant; and
a vent communicating the first region of the interior space to a location outside the chamber.

Preferably the barrier is defined by a secondary enclosure of smaller size than said interior space of the chamber, said secondary enclosure being situated within the chamber to delimit the first region within said secondary enclosure.

According to a second aspect of the invention, there is provided a method of performing gas exchange analysis on a whole plant canopy, the method comprising:
(a) enclosing a whole plant within a chamber;
(b) using a barrier to separate a first region of said interior space that contains a growth medium in which said whole plant is rooted from a second region of said interior space that contains a canopy of said whole plant;
(c) using incoming air entering the interior space at the second region thereof to maintain said second region in a pressurized state;
(d) venting the first region to a location outside the chamber, wherein pressurization of the second region relative to the vented first region prevents leakage or escape of air from the first region into the second region, thereby minimizing effects of the growth medium and roots of the plant on measurements made on a separate outgoing air flow from the second region to a gas sensor.

According to a third aspect of the invention, there is provided a kit for use in gas exchange analysis on a whole plant canopy, said kit comprising:
a chamber having an interior space arranged to contain a whole plant and an associated growth medium therein, said interior space including a first region for accommodating said growth medium and a root system of said whole plant established within said growth medium, and a second region for accommodating a canopy of said whole plant;

a secondary enclosure of smaller size than said interior space of the chamber, said secondary enclosure being placeable within the chamber to delimit the first region within confines of said secondary enclosure, and said secondary enclosure having an opening through which a stem of said whole plant is receivable to transition between the first and second regions of the interior space of the chamber; and a vent line operatively connectable to the secondary enclosure to vent the first region of the interior space to a location outside the chamber.

BRIEF DESCRIPTION OF THE DRAWINGS

One embodiment of the invention will now be described in conjunction with the accompanying drawings in which.

In the drawings like characters of reference indicate corresponding parts in the different figures.

DETAILED DESCRIPTION

Figure 1:
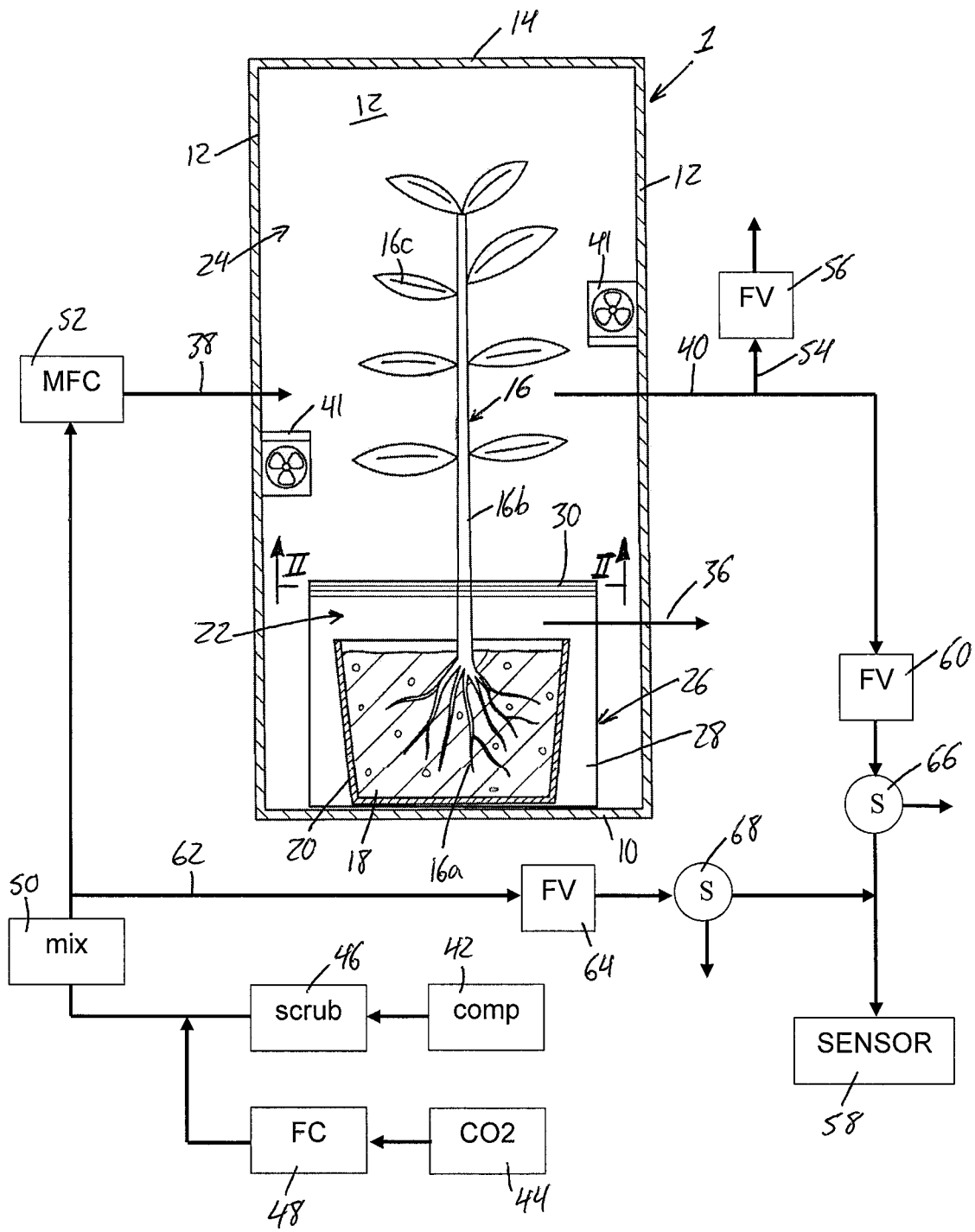
FIG. 1 is a schematic illustration of a whole-plant gas exchange system featuring a whole-plant chamber in which a vented secondary enclosure closes substantially around the potted soil and roots of the plant to separate same from a pressurized remainder of the enclosure so that the effects of soil and root respiration are isolated from gas exchange measurements concerning the plant canopy.

The whole plant gas exchange system of FIG. 1 features a whole plant chamber 1 comprising a horizontal base 10, a series of upright walls 12 standing upward from the base around the perimeter thereof, and a top wall 14 spanning horizontally between the upright walls at the top end thereof. The upright walls and top wall, and optionally the base, are formed of acrylic or other substantially transparent and air impermeable material capable of allowing light transmission into the interior space bound by the base and walls. This light transmissibility enables photosynthesis by a plant 16 disposed within this interior space of the chamber 10 using external light sources in the environment outside the chamber. Another embodiment may one or more opaque walls (e.g. of metal or plastic construction) in combination with at least one transparent wall to admit light into the chamber from an external light source. Other embodiments may employ opaque or translucent materials for the walls and rely on an internal light source within the chamber. Access to the interior space of the chamber to enable placement and removable of the plant therein and therefrom may be enabled by any suitable means, for example an openable door or removal panel on one of the upright walls that is closeable in an airtight manner. In another example, the top wall may be removable or openable, while in yet another example, upright and top walls lacking access doors or panels may be affixed to one another but removal from the base, whereby the fixed-together walls forms a removable cover that can be lifted from the base to access the chamber interior.

The illustrated plant 16 is a potted plant whose roots 16a are embedded within a volume of soil 18 contained within a conventional open-top planting pot 20. A canopy of the plant is made up of all parts of the plant located above the soil surface, which in the illustrated example includes a singular main stem 16b standing upright from the surface of the potted soil 18, and a plurality of leaves 16c carried on the stem. The system differs from the prior art primarily in the way in which the gas-exchange effects of the soil and roots of the plant on the air inside the chamber are isolated from the effects of the canopy's photosynthetic interaction with said air so that accurate measurement of the gas exchange taking place specifically between the canopy and the air can be performed with significant accuracy.

Instead of a rigid divider separating the interior space of the chamber into separate compartments of fixed predetermined size, the chamber of the illustrated embodiment is separated into two regions or zones 22, 24 by a smaller secondary enclosure 26 made of air impermeable material and placed within the interior space of the larger outer chamber 1. In the case of the illustrated embodiment, the smaller secondary enclosure 26 is a flexible plastic bag 28 of a conventional commercially available type that has a selectively openable and closeable zipper closure 30 at one end thereof, and is otherwise closed on all sides of the bag. With the bag open and in a normal upright orientation placing the zippered closure 30 at the top end of the bag, the planting pot 20 is placed inside the plastic bag 28 in a normal upright position so that the plant stem 16b reaches upwardly through the open top end of the bag 28, and the bagged pot 20 is then seated atop the base 10 of the chamber 1. Accordingly, the bag spans fully around the outer circumferential wall of the pot 20, and also fully spans the underside of the pot 20 in a position sandwiched between the base of the chamber and the pot's bottom wall. The entirety of the planting pot and the soil and roots contained therein are thus contained within the confines of the air-impermeable walls of the plastic bag.

Figure 2:
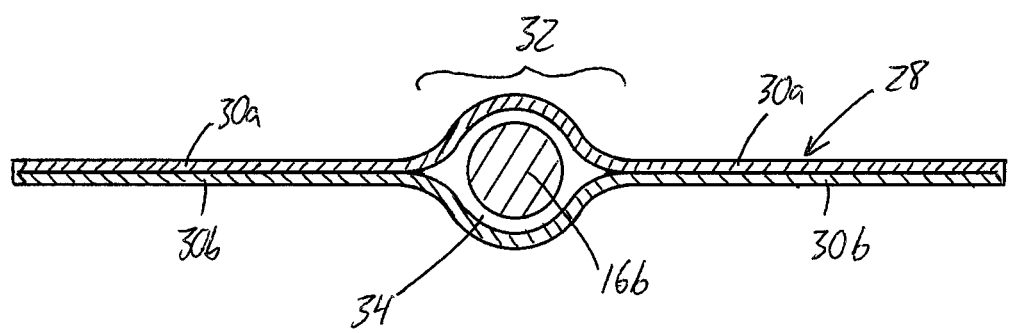
FIG. 2 is a cross-sectional view of the plant stem and secondary enclosure of FIG. 1 as taken along line II-II thereof to illustrate passage of the plant stem through a partially closed zipper closure at the top end of the secondary enclosure.

To further enclose the pot 20, soil 18 and roots 16a within the confines of the bag, the zipper closure 30 at the top end of the bag may be partially closed, thereby reducing the size of the opening at the top end of the bag to more closely close around the stem 16b of the plant. In the illustrated example, the singular stem 16b of the plant is situated generally centrally along the zippered top end of the bag 28, and so the zippered closure is preferably closed on both sides of the plant stem 16b, leaving only a central area of the zipper closure in an open state around the periphery of the plant stem. FIG. 2 illustrates this partial closure of the top end of the bag 28 around the plant stem 16b, whereby on two diametrically opposing sides of the stem 16b, the two matable zipper elements 30a, 30b at the top ends of two opposing sides of the bag 28 are engaged together in a closed state, but remain separated from one another at a central area 32 of the closure so as to leave an open annular space 34 between the plant stem and the bag 28. The zipper elements 30a, 30b provide air-tight closure of the bag's top end where they are mated together on opposing sides of the plant stem, leaving only the small annular space around the plant stem as the only open space through which the two regions of the chamber's interior space are communicated with one another, as the regions are otherwise separated in an airtight manner by the air impermeable walls of the bag and the sealed closed areas of the zipper closure.

Turning back to FIG. 1, the interior of the bag denotes the first region or zone 22 of the chamber interior in which the soil and roots are contained, while the remaining space of the chamber interior outside the bag 28 denotes the second region 24 or zone in which a substantial majority of the plant canopy is contained. The top end of the bag 28 is preferably closed around the plant stem in close relation to both the top rim of the pot 20 and the surface of the soil situated shortly therebelow. Accordingly, the amount of plant stem disposed inside the bag 28 is kept to a minimum in order to maximize the substantial majority of the stem that resides outside the bag in the second region of the chamber interior. Likewise, the closing of the bag in close relation to the soil surface at or near the top end of the pot maximizes the percentage of leaves residing in the second region, preferably so that all of the leaves are contained therein. Accordingly, substantially the entire canopy of the plant resides in the second region, which maximizes the accuracy of canopy-related measurements made by the system.

The first region 22 inside the flexible bag 28 has a vent line, schematically illustrated at 36, that communicates this space with the ambient environment at a location outside the chamber. The vent line may be formed from flexible tubing or rigid pipe that runs from through a side wall of the bag and onwardly through a corresponding upright wall 12 of the chamber. Suitable sealant between the exterior of the vent line and the bag and chamber walls is used to prevent air leaks at each transition of the vent conduit from one space to another, thereby maintaining the air-tightness of the overall chamber and the air-impermeability of the bagged closure of the plant roots and soil. The vent line may discharge directly to the ambient environment, as shown in the drawings, or indirectly to the ambient environment through one or more pieces of external equipment, for example through a gas measurement/monitoring system.

The second region 24 of the chamber interior has an air intake line, schematically illustrated at 38, that opens into the interior of the chamber at this second region 24 through one of the upright walls 12 of the chamber to enable introduction of incoming air thereto. The second region 24 of the chamber interior likewise has an air outlet line, schematically illustrated at 40, that opens into the interior of the chamber at this second region 24 through one of the upright walls 12 of the chamber to enable exit of outgoing air therefrom. Each of the air intake and outlet lines may be defined by a respective conduit formed from flexible tubing or rigid pipe that runs from through a side wall of the chamber in a suitably sealed airtight manner. As shown, the air intake and outlet lines may be situated in opposing chamber walls to maximize the distance therebetween, and one or more circulation fans 41 may be mounted within the second region of the chamber interior to encourage uniform mixing of the incoming air throughout the second region. This measure helps prevent the incoming air from flowing directly to the air outlet line and bypassing significant exposure to the plant canopy.

The air intake line 38 is fed by an air supply circuit including a pressurized air source 42, such as an air compressor or blower, and a carbon dioxide supply 44, such as a pressurized $CO_2$ cylinder, for controlling the carbon dioxide concentration in the incoming air. As shown, the pressurized air source 42 may be connected to a scrubber 46 for removing carbon dioxide from ambient air prior to controlled introduction of carbon dioxide to the scrubbed air from the pressurized carbon dioxide supply by a flow controller 48. This may provide improved control over the incoming air characteristics compared to use of unscrubbed ambient air. In such cases, a mixing chamber 50 is preferably included downstream of the flow controller's introduction of carbon dioxide to the pressurized airflow, whereby a more uniform carbon dioxide concentration is attained. A mass flow controller 52 is situated downstream of the mixing chamber 50 to provide careful control over the mass flow rate of incoming air entering the second region of the plant chamber interior through the air intake line 38.

Outside the chamber, the air outlet line 40 has an exhaust branch 54 through which a portion of the outgoing air stream can be vented to the ambient environment through a flow valve 56. Downstream of the exhaust branch 54, the air outlet line 40 feeds into a gas analyzation sensor 58 via another flow valve 60. The gas sensor is operable to measure the carbon dioxide concentration in the outgoing air from the chamber. In the illustrated embodiment, the same sensor 58 may be used to measure the carbon dioxide concentration of the incoming air entering the chamber at a location downstream of the mixing chamber 50 and upstream where the air inlet line opens into the chamber interior. For this purpose, an intake sampling line 62 branches off the inlet line 38 between the mixing chamber 50 and the mass flow controller 52 and feeds into the gas sensor via another flow valve 64. A respective solenoid valve 66/68 is disposed between the gas sensor 58 and the flow valve 60/64 on each of the outlet and sampling lines 60, 62. In a first or 'closed' state, each solenoid closes off flow to the sensor, and instead vents the respective line to the ambient environment. In a second or 'open' state, the solenoid closes off the vent port and instead opens up flow to the gas sensor. Accordingly, altering which of these two solenoids is open at any time controls which one of the two lines is feeding the sensor. The same sensor is thus operable to analyze both the incoming and outgoing air of the chamber to enable differential measurement of the carbon dioxide concentration of the outgoing air versus the incoming air in order to effectively measure carbon dioxide consumption within the second region of the chamber. Sharing of a singular sensor for both the pre-chamber and post-chamber air analysis reduces the overall system cost and also provides increased accuracy in the case of differential measurement, though two different sensors could alternatively be used. It will be appreciated that the air supply and air analyzation circuits respectively supplying and receiving the incoming and outgoing air streams of the chamber may vary from the particular example set forth in the illustration embodiment without detracting from the unique use of the vented secondary enclosure 26 and pressurization of the chamber to isolate the effects of the soil and roots from the plant canopy measurements.

The incoming air enters the chamber through the air inlet line 38, thus specifically feeding into the second region of the chamber at a location outside the flexibly enclosed interior of the plastic bag. The second region of the chamber is interior is maintained in a pressurized state. For example, initially the air supply circuit is operated with the flow valves of the air outlet line fully closed and with the vent line of the secondary enclosure blocked off in order to raise the pressure of the chamber interior to above atmospheric pressure, at which point the vent line is re-opened and the flow valves of the air outlet are opened in a controlled manner to a suitable positions cooperable with the ongoing flow of incoming air to maintain the pressurized state inside the chamber interior, while enabling suitable flow of the outgoing air to the gas sensor. Since the first region inside the bag is vented to atmosphere, the pressurization of the second region to above-atmospheric pressure values means that any air exchange between bag-enclosed first region and the surrounding second region involves only the passage of incoming air from the second region into the atmospherically vented first region. That is, the pressurized state allows air from the second region to enter the bag via any open space between the plant stem and the bag at the at least partially closed upper end of the bag, but prevents any backflow of air from the interior of the bag back into the surrounding areas of the chamber. The air inside the bagged second region can only exit the bag through the vent line. Accordingly, air inside the bag is actively prevented from entering the second region, whereby carbon dioxide release from the soil and carbon dioxide absorption by the plant roots will not affect measurement of the plant canopy's gas exchange.

It will be appreciated that similar use of a pressurized canopy region and separately vented soil-root region inside the chamber interior could be achieved using means other than a flexible plastic bag to provide the physical separation between these two regions. However, this use of a bag that is separate from and fully independent of the chamber base and walls provides potential advantages over prior art designs with rigid compartment dividers built into the chamber design itself. Plants and pots of varying size can be easily adjusted for by use of differently sized plastic bags. Placement of the plant's potted roots inside plastic bag and partial closing of the bag around the plant stem exceeds the ease of assembling a multi-segment chamber divider around a plant stem and applying a sealant around the stem. Alternatively, a While the illustrated plant has a semi-rigid upright main stem reaching into upper areas of the chamber, the plastic bag also allows for use of less-erect plants whose canopies can hang down over the exterior of the bag due to the fact that the second canopy-containing region of the chamber interior spans down to the base of the chamber around the exterior of the bag. The flexibility of the bag allows the size and shape of the root and soil containing second region to be varied by flexing of the bag walls to vary the shape and dimensions of the bag. Zipper-closure bags provide an easy solution for adjusting the opening-size at the top of the bag. This may be useful to accommodate plants of varying stem size, and/or to minimize the open air space around the plant stem at the bag closure while having the option of avoiding physical contact between the stem and bag. Use of such non-conforming openings with non-elasticized boundaries that do not self-tighten against the circumference of the stem may be beneficial, for example to avoid potential damage or stress to the plant that might result from a tight circumferential fit around the plant stem. However, other solutions for fully or partially closing a bag around the plant stem may be employed, for example including use of a drawstring-adjustable bag closure, use of an elasticized bag opening stretchable around the pot and self-reducing in size to reach inwardly over the top end of the pot toward the plant stem, or use of a separate band (elastic or sizeable) to cinch the band closed around the stem.

While the illustrated embodiment features a potted plant employing soil as the growing medium, the similar use of an air impermeable barrier between a vented root region and pressurized canopy region may be used regardless of whether the growth medium is soil, and regardless of whether the growth medium is contained within a pot. For example, the growth medium, whether soil or otherwise, could instead be contained solely by the secondary closure. That is, a plant could be planted inside a bag or other type of secondary enclosure that is later placed inside the chamber. Accordingly, the pot itself may be formed of air-impermeable, or at least $CO_2$ impermeable material, and may form part of the secondary enclosure, for example being equipped with a lid or cover (e.g. air/$CO_2$ impermeable film or membrane) to cover the soil in a position surrounding the plant stem.

While the illustrated embodiment employs a flexible bag of air-impermeable plastic material to define a secondary enclosure forming a barrier between the two regions, it will be appreciated that the isolation of the root and soil respiration requires only that the enclosure/barrier material be impermeable to at least $CO_2$. Accordingly, materials preventing $CO_2$ transfer thereacross while admitting passage of other substances therethrough would still be useful as the secondary enclosure or barrier. In addition, the secondary enclosure need not necessary be flexible, and for example could be in the form of a rigid or semi-rigid box having air-impermeable, or at least $CO_2$ impermeable, walls, with an air/$CO_2$ impermeable lid or cover (e.g. membrane or film) fitted over the top end of the box and having a suitable stem-accommodating opening therein. In the case where the secondary enclosure features a pot or box with a cover or lid fitted thereover to enclose the soil, the seed of the plant may be planted in the soil through an opening in the cover or lid, through which the plant subsequently grows.

Since various modifications can be made in the invention as herein above described, and many apparently widely different embodiments of same made within the scope of the claims without departure from such scope, it is intended that all matter contained in the accompanying specification shall be interpreted as illustrative only and not in a limiting sense.

The invention claimed is:

1. A whole plant gas exchange apparatus comprising:
   a chamber having an interior space containing, or arranged to contain, a whole plant and an associated growth medium therein, said interior space including a first region for accommodating said growth medium and a root system of said whole plant established within said growth medium, and a second region for accommodating a canopy of said whole plant;
   a barrier separating said first and second regions of the interior space from one another;
   an opening between the first and second regions of the interior space to accommodate receipt of a stem of said whole plant through said opening to reach from the root system in the first region to the canopy in the second region;
   an air intake feeding into the interior space of the chamber only at the second region thereof;
   an air source connected to the air intake to introduce air into the interior space only within the second region thereof;
   an air outlet communicating with only the second region of the interior space to convey outgoing air from the second region to a gas sensor for analysis of said outgoing air after photosynthetic interaction with the canopy of the whole plant; and
   a vent communicating the first region of the interior space to a location outside the chamber;
   wherein the first region of the interior space lacks any air intake feeding thereinto from outside the chamber, and the air source, air intake and air outlet are cooperatively configured such that air is fed into the interior space at only the second region thereof and pressurizes the second region relative to the first region at a positive pressure relative to an immediately surrounding ambient environment in which the chamber resides.

2. The apparatus of claim 1 wherein the barrier is defined by a secondary enclosure of smaller size than said interior space of the chamber, said secondary enclosure being situated within the chamber to delimit the first region within said secondary enclosure.

3. The gas exchange chamber of claim 2 secondary enclosure is adjustable in shape or size to adjust a relative size of the first region of the interior space relative to the second region thereof.

4. The gas exchange chamber of claim 1 wherein the opening is a non-conforming opening by which some of the incoming air can enter the first region through space between the barrier and the stem of the whole plant.

5. The gas exchange chamber of claim 1 wherein the opening is adjustable in size.

6. The gas exchange chamber of claim 1 wherein the opening has a non-elasticized boundary.

7. The gas exchange chamber of claim 1 wherein the barrier comprises a flexible bag for containing the root system and the growth medium therein.

8. The gas exchange chamber of claim 1 wherein the barrier comprises a zippered closure around the opening, whereby said zippered closure is partially closeable to reduce a size of the opening around the stem of the plant.

9. The gas exchange chamber of claim 1 wherein the first region is free of any other inlets or outlets other than the vent and the opening.

10. The gas exchange chamber of claim 1 wherein the air inlet feeding into the interior space in only the first region thereof is the only source of incoming air to the chamber.

11. The apparatus of claim 1 wherein the barrier is flexible.

12. A method of performing gas exchange analysis on a whole plant canopy, the method comprising:
    (a) enclosing a whole plant within a chamber;
    (b) using a barrier to separate a first region of said interior space that contains a growth medium in which said whole plant is rooted from a second region of said interior space that contains a canopy of said whole plant;
    (c) using incoming air entering the interior space at only the second region thereof, and simultaneous venting of air from the first region thereof to a location outside the chamber, to maintain said second region in a pressurized state relative to the first region and at a positive pressure relative to an immediately surrounding ambient environment in which the chamber resides;
    whereby pressurization of the second region relative to the vented first region prevents leakage or escape of air from the first region into the second region, thereby minimizing effects of the growth medium and roots of the plant on measurements made on a separate outgoing air flow from the second region to a gas sensor.

13. The method of claim 12 wherein step (b) comprises disposing the plant growth medium within a secondary enclosure inside the chamber.

14. The method of claim 13 wherein the secondary enclosure is a flexible bag.

15. The method of claim 13 wherein step (b) comprises disposing a pot in which the plant growth medium is contained within the secondary enclosure.

16. The method of claim 13 comprising selecting the secondary enclosure from among a plurality of differently sized enclosures according to characteristics of the whole plant concerned.

17. The method of claim 12 wherein step (b) comprises leaving open space between a stem of the plant and the barrier at an opening of said barrier through which the stem of the plant reaches from the first region into the second region.

18. The method of claim 12 wherein step (b) comprises adjusting a size of an opening between the first and second regions in order to adjust a fit of said barrier around a stem of the plant that reaches from the first region into the second region through said opening.

19. The method of claim 17 comprises configuring the opening to keep the barrier and the plant stem free of contact with one another.

* * * * *